United States Patent
Van Nguyen et al.

(10) Patent No.: US 6,800,277 B2
(45) Date of Patent: Oct. 5, 2004

(54) HAIR RELAXER COMPOSITIONS WITH A VISUAL INDICATOR

(75) Inventors: Nghi Van Nguyen, Edison, NJ (US); David W. Cannell, Plainfield, NJ (US)

(73) Assignee: L'Oreal, S.A. (FR)

( * ) Notice: Subject to any disclaimer, the term of this patent is extended or adjusted under 35 U.S.C. 154(b) by 112 days.

(21) Appl. No.: 10/183,431

(22) Filed: Jun. 28, 2002

(65) Prior Publication Data

US 2004/0005284 A1 Jan. 8, 2004

(51) Int. Cl.$^7$ ................................................ A61K 7/09
(52) U.S. Cl. ..................................... 424/70.2; 424/70.1
(58) Field of Search ................................ 424/70.1, 70.2

(56) References Cited

U.S. PATENT DOCUMENTS

| | | |
|---|---|---|
| 4,304,244 A | 12/1981 | de la Guardia |
| 5,077,042 A | 12/1991 | Darkwa et al. |
| 5,565,216 A | 10/1996 | Cowsar et al. |
| 5,679,327 A | 10/1997 | Darkwa et al. |
| 5,849,277 A | 12/1998 | Cowsar |

*Primary Examiner*—Jyothsna Venkat
(74) *Attorney, Agent, or Firm*—Finnegan, Henderson, Farabow, Garrett & Dunner, L.L.P.

(57) ABSTRACT

A method for lanthionizing keratin fibers to achieve relaxation of said keratin fibers and multicomponent kits for lanthionizing keratin fibers to achieve relaxation of the keratin fibers are also provided.

36 Claims, No Drawings

HAIR RELAXER COMPOSITIONS WITH A VISUAL INDICATOR

The present invention relates to methods for lanthionizing keratin fibers using a combination of at least one carbonate compound, at least one chelating acid, and at least one hydroxide compound. The at least one chelating acid can react with the at least one carbonate compound to effect generation of carbonic acid gas and a chelating compound. In one embodiment, the process of lanthionizing keratin fibers may result in relaxed, including straightened, hair. The invention is also directed to multicomponent kits for relaxing, including straightening, hair comprising at least one carbonate compound, at least one chelating acid, and at least one hydroxide compound.

Straightening or relaxing the curls of very curly hair may increase the manageability and the ease of styling such hair. In today's market, there is an increasing demand for hair care products referred to as "hair relaxers" which can relax or straighten naturally curly or kinky hair. Hair relaxers may either be applied in a hair salon by a professional or in the home by the individual consumer.

Hair fiber is a keratinous material which is comprised of proteins. Many of the polypeptides in hair fibers are bonded together by disulfide bonds (—S—S—). A disulfide bond may be formed from the reaction of the two sulfhydryl groups (—SH) one on each of two cysteine residues which results in the formation of a cystine residue. While there may be other types of bonds between the polypeptides in hair fibers, such as ionic bonds, the permanent curling and the shape of the hair is essentially dependent on the disulfide bonds of cystine residues.

Generally, hair relaxing processes are chemical processes which may alter the aforementioned disulfide bonds between polypeptides in hair fibers and may form lanthionine residues $[S[CH_2CH(NH—)(CO—)]_2]$. Thus, the term "lanthionizing" is used when one skilled in the art refers to the relaxing, including straightening, of keratin fibers by hydroxide ions.

For example, hair fibers may be relaxed or straightened by disrupting the disulfide bonds of the hair fibers with an alkaline reducing agent. The chemical disruption of disulfide bonds with such an agent is generally combined with mechanical straightening of the hair, such as combing, and straightening generally occurs due to changes in the relative positions of neighboring polypeptide chains within the hair fiber.

This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. One reaction sequence comprises at least one bimolecular nucleophilic substitution reaction wherein an available hydroxide ion directly attacks the disulfide linkage of a cystine residue. The result is the formation of lanthionine residues and $HOS^-$. See Zviak, C., *The Science of Hair Care*, 185–186 (1986). The second reaction sequence comprises at least one β-elimination reaction initiated by the nucleophilic attack of an available hydroxide ion on a hydrogen atom bonded to a carbon atom that is in the β-position with respect to the disulfide bond of a cystine residue. See Zviak. The result is the formation of a dehydroalanine residue. The dehydroalanine residue then reacts with either the thiol group of a cysteine residue or the amino group of an alanine residue to form a lanthionine residue or a lysinoalanine residue, respectively. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid and minimize damage to the hair protein or skin. If such a step is required, an acidic shampoo may be used to neutralize residual alkali and remove it from the hair and scalp.

Hydroxide-containing alkaline agents also have other advantages. For example, alkaline agents, such as guanidine hydroxide, do not have a highly objectionable odor or cause such an odor on treating the hair. Further, hydroxide-based straighteners generally have relatively fast processing times and good relaxation of naturally curly or kinky hair. Additionally, the achieved relaxing effect is more permanent; i.e., less likely to revert to a curly state after shampooing and wearing than is hair relaxed with some other relaxers.

Despite these advantages, certain hydroxide-containing alkaline agents may have disadvantages. These disadvantages may be heightened when the hydroxide-containing alkaline agent is sodium hydroxide. Specifically, the causticity of sodium hydroxide can adversely affect the condition of the hair, for example, leaving it in a brittle state and harsh to the touch. Additionally, prolonged or unnecessary exposure of hair to such a strong alkali can weaken, break and dissolve the hair. In some instances, such a strong alkali can discolor the natural color of the hair. For example, the tone of natural brown hair may be reddened and natural white or grey hair may be yellowed. Further, the natural sheen of the hair may be delustered.

Most frequently, commercial relaxing compositions are in the form of gels or emulsions that contain varying proportions of strong water-soluble bases, such as sodium hydroxide (NaOH), or of compositions that contain slightly-soluble metal hydroxides, such as calcium hydroxide ($Ca(OH)_2$), which can be converted in situ to soluble bases, such as guanidine hydroxide. Traditionally, the two main hair relaxers used in the hair care industry for generating hydroxide ions are referred to as "lye" (lye=sodium hydroxide) relaxers and "no lye" relaxers.

The "lye" relaxers generally comprise sodium hydroxide in a concentration ranging from 1.5% to 2.5% by weight relative to the total weight of the composition (0.38M–0.63M) depending on the carrier used, the condition of the hair fibers and the desired length of time for the relaxation process.

While "no lye" relaxers may not contain lye, they may nonetheless rely on the soluble hydroxides of inorganic metals, such as potassium hydroxide and lithium hydroxide. Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

In commercial products based on guanidine hydroxide, the concentration of guanidine carbonate used is generally at least 5.8% by weight relative to the total weight of the final mixture. Significantly, it is known that relaxers derived from guanidinium hydroxide are inherently less irritating to the skin and scalp than those deriving from alkali metal hydroxides. See U.S. Pat. No. 5,849,277, the disclosure of which is incorporated herein by reference.

Although generally gentler on the hair, guanidine carbonate and calcium hydroxide may create a different set of problems. The insoluble byproduct, $CaCO_3$, can leave a white residue or unattractive "whitening" or "ashing." This residue remains in the hair since divalent metals such as calcium have a relatively good affinity for keratin. A decalcifying shampoo may be subsequently needed to remove the ashing.

This ashing may be especially problematic when using strong commercial hair relaxers which generally comprise a high concentration of both guanidine carbonate and calcium hydroxide. For example, according to U.S. Pat. No. 5,679,327, the disclosure of which is incorporated herein by reference, to achieve permanent hair relaxation, for example of coarse and resistant hair, the amount of calcium hydroxide should generally range from 4% to 10% by weight and the amount of guanidine carbonate should generally be 28% by weight.

Thus, there is still a need for a process to relax keratin fibers gently that has the advantages of using an insoluble metal hydroxide, such as $Ca(OH)_2$, but reduces or eliminates the problem of ashing caused by the insoluble byproduct, $CaCO_3$.

Accordingly, the present invention provides a method for lanthionizing keratin fibers to achieve relaxation of the keratin fibers comprising generating a composition comprising at least one chelating compound by reacting at least one carbonate compound and at least one chelating acid, wherein the molar ratio of the chelating acid to the carbonate compound is greater than 0.2:1; generating at least one activated hydroxide composition by reacting the composition comprising at least one chelating compound with at least one hydroxide compound; applying the at least one activated hydroxide composition to the keratin fibers for a sufficient period of time to lanthionize the keratin fibers; and terminating the lanthionization. In one embodiment, the at least one hydroxide compound is reacted with the composition comprising at least one chelating compound following release of carbonic acid gas formed from the reaction of the at least one carbonate compound and the at least one chelating acid.

As used herein, "at least one" means one or more and thus includes individual components as well as mixtures/combinations. Further, as used herein, "keratin fibers" as defined herein may be human keratin fibers, and may be chosen from, for example, hair.

The present invention is also drawn to a method of generating an activated hydroxide compound comprising generating a composition comprising at least one chelating compound by reacting at least one carbonate compound and at least one chelating acid, wherein the molar ratio of the at least one chelating acid to the at least one carbonate compound is greater than 0.2:1, and reacting the composition comprising at least one chelating compound with at least one hydroxide compound.

The present invention is also drawn to a multicomponent kit for lanthionizing keratin fibers comprising at least two compartments, wherein a first compartment comprises at least one carbonate compound and at least one chelating acid, wherein the molar ratio of the at least one chelating acid to the at least one carbonate compound greater than 0.2:1; and wherein a second compartment comprises at least one hydroxide compound.

Another embodiment of the invention relates to a multicomponent kit for lanthionizing keratin fibers comprising at least three compartments, wherein a first compartment comprises at least one carbonate compound; wherein a second compartment comprises at least one chelating acid; and wherein a third compartment comprises at least one hydroxide compound.

Reference will now be made in detail to exemplary embodiments of the present invention. Not to be limited as to theory, the lanthionization of keratin fibers is believed to be driven by the release of hydroxide ions, which disrupt the disulfide bonds of cystine. The compositions of the present invention offer advantages over traditional "lye" or "no-lye" hair relaxers by providing a novel way of generating soluble hydroxide ions from hydroxide compounds while still being effective to relax or straighten the hair.

As used herein, a compound or composition "reacts" with another compound or composition when their combination effects a chemical change in at least one of the compound or composition and the other compound or composition, such as, for example, interacts with the other compound or composition via formation and/or breaking at least one bond chosen from hydrophobic bonds, ionic bonds, and covalent bonds.

As described above, the hair relaxing compositions of the prior art utilized soluble metal hydroxides or slightly soluble metal hydroxides. Slightly soluble metal hydroxides, including most divalent metal hydroxides, are not soluble enough in water to generate sufficient soluble hydroxide ions to effect lanthionization of keratin fibers. This can be represented by the following, in which the equilibrium favors the left side of the reaction:

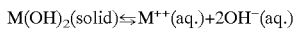

$$M(OH)_2(solid) \rightleftharpoons M^{++}(aq.) + 2OH^-(aq.)$$

Therefore, in traditional relaxers containing slightly soluble metal hydroxides, the equilibrium was pushed to the right side and the reactions driven to completion by the precipitation of $M^{++}$ as an insoluble compound such as $CaCO_3$.

The compositions of the present invention, however, utilize at least one chelating acid to react with at least one carbonate compound, such as guanidine carbonate. As a result of this reaction, a chelating compound and carbonic acid gas are formed. The carbonic acid gas acts as a visual indicator letting one know when the chelating compound (such as a guanidinium chelate) is forming. A composition comprising the at least one chelating compound is combined with a hydroxide compound, such as calcium hydroxide, which may be comprised in at least one hydroxide composition to generate at least one activated hydroxide compound, such as guanidine hydroxide, and a soluble by-product, such as a calcium chelate.

An example of these reactions can be represented by the following:

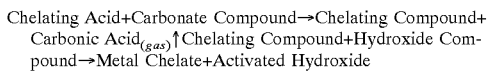

Chelating Acid+Carbonate Compound→Chelating Compound+ Carbonic Acid$_{(gas)}$↑ Chelating Compound+Hydroxide Compound→Metal Chelate+Activated Hydroxide The at least one chelating acid allows the equilibrium in the first reaction to be shifted to the right. In other words, the at least one chelating acid may react with the carbonate compound, thereby allowing visual indication of the formation of the chelating compound. In one embodiment, once the bubbling of the composition has stopped (e.g., a majority of the carbonic acid gas has been liberated), the composition comprising the resulting chelating compound may be combined with at least one hydroxide compound to generate an activated hydroxide compound. Of course, the composition comprising the resulting chelating compound may be combined with the at least one hydroxide compound before bubbling has stopped if a smaller amount of chelating compound is desired.

The inventive process therefore involves two buffer systems. One buffer is a carbonate/bicarbonate buffer which results from reaction of the chelating acid with the carbonate compound, and can be represented by the following reactions:

The second buffer is a chelating acid/chelating compound buffer, such as a citric acid/citrate buffer, which results from the reaction of the chelating acid with a base (the carbonate compound and/or hydroxide compound), and can be represented by the following reaction:

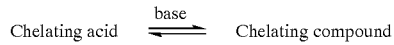

Accordingly, the two buffer systems help regulate the pH of the lanthionizing composition which is applied to keratin fibers, that is, the composition comprising at least one activated hydroxide compound, by controlling the release of the available hydroxide ions, i.e., by keeping the composition from becoming too "hot." When the carbonate compound is combined with the chelating acid, the composition may generally have a pH of around 6. In the absence of the above buffer systems, the pH of the composition would be expected to be around 10. Thus, according to the present invention, any subsequent increase in the concentration of hydroxide ions must initially overcome the buffer capacity of these two buffers.

The inventors have found that, in one embodiment, when a composition comprising at least one chelating compound is combined with at least one hydroxide compound, the pH of the resultant mixture increases slowly to between 13 and 13.7. This gradual increase is believed to indicate a continuous shift to the right in the equilibrium of the chelating acid/chelating compound buffer. As this equilibrium is shifted to the right, a higher concentration of chelating compound results. This chelating compound can react with the at least one hydroxide compound to slowly but continuously form at least one activated hydroxide compound. Thus, the release of available hydroxide ions is controlled by the kinetics of the chelating acid/chelating compound buffer reaction.

The net effect of the two buffer systems may be the control of the causticity of the lanthionizing composition (the compositions comprising at least one activated hydroxide compound) and this may thereby prevent the composition from becoming too "hot" too quickly. This control results in milder lanthionization of keratin fibers than that obtained using commercially available relaxer compositions which, in turn, results in less irritation to the skin and scalp.

Yet another advantage of the present invention is the reduction, including elimination, of ashing. As previously mentioned, lanthionizing compositions comprising guanidine carbonate and calcium hydroxide may leave a white residue or unattractive "whitening" or "ashing" because of the insoluble byproduct, $CaCO_3$, that is formed. In contrast, a soluble by-product, a calcium chelate, results when a chelating compound and calcium hydroxide are used in the method of the present invention.

According to the present invention, the at least one hydroxide compound is chosen from hydroxide compounds comprising at least one cationic counterion which is capable of being complexed, chelated, sequestered or otherwise tied up by the at least one chelating compound. The at least one hydroxide compound may be chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable which comprise at least one cationic counterion which is capable of being complexed, chelated, sequestered or otherwise tied up the at least one chelating compound. In one embodiment, the at least one hydroxide compound is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide. In another embodiment, the at least one hydroxide compound is chosen from calcium hydroxide.

According to the present invention, the molar ratio of the at least one chelating acid to the at least one hydroxide compound is at least 1:0.2. As used herein, (i.e., throughout the specification), "at least" includes the values recited, whereas "greater than" does not. In one embodiment, the molar ratio of the at least one chelating acid to the at least one hydroxide compound is at least 1:0.3, such as greater than 1:0.3. In one embodiment, the molar ratio of the at least one chelating acid to the at least one hydroxide compound is at least 1:0.4, such as greater than 1:0.4, while in another embodiment, the molar ratio of the at least one chelating acid to the at least one hydroxide compound is at least 1:0.5, such as greater than 1:0.5. In another embodiment, the molar ratio of the at least one chelating acid to the at least one hydroxide compound is at least 1:0.6, such as greater than 1:0.6, and in another embodiment, the molar ratio of the at least one chelating acid to the at least one hydroxide compound is at least 1:0.7, such as greater than 1:0.7. In another embodiment, the molar ratio of the at least one chelating acid to the at least one hydroxide compound is at least 1:0.8, such as greater than 1:0.8, and in another embodiment, the molar ratio of the at least one chelating acid to the at least one hydroxide compound is at least 1:0.9, such as greater than 1:0.9. In one embodiment, the molar ratio of the at least one chelating acid to the at least one hydroxide compound is at least 1:1, such as greater than 1:1, and further such as at least 1:1.2. In one embodiment, the molar ratio of the at least one chelating acid to the at least one hydroxide compound is less than 1:1. In one embodiment, the molar ratio of the at least one chelating acid to the at least one hydroxide compound is 1:1. In one embodiment, the molar ratio of the at least one chelating acid to the at least one hydroxide compound is less than 1:2 and all points in between 1:2 and 1:1.

According to the present invention, the at least one hydroxide compound may be comprised in at least one hydroxide composition. The at least one hydroxide composition may be in the form of a solution, an emulsion, a suspension, a solid, a cream, a gel, a paste or a foam.

The at least one hydroxide composition may further comprise at least one suitable additive chosen from additives commonly used in hair relaxing compositions. Non-limiting examples of the at least one additive include solvents, anionic surfactants, cationic surfactants, nonionic surfactants, amphoteric surfactants, zwitterionic surfactants, thiol compounds, fragrances, silicones, silicone derivatives, screening agents, preserving agents, proteins, vitamins, polymers such as thickening polymers, plant oils, mineral oils, synthetic oils and any other additive conventionally used in compositions applied to keratinous fiber. Non-limiting examples of suitable solvents include water and organic solvents. Non-limiting examples of organic solvents include alkanols, such as ethanol, isopropanol, and ceteryl alcohol; glycerol; glycols and glycol ethers, such as 2-butoxyethanol, propylene glycol, propylene glycol monomethyl ether, diethylene glycol monoethyl and monomethyl ether, and aromatic alcohols, such as benzyl alcohol and phenoxyethanol, and mixtures thereof.

When at least one hydroxide composition comprises the at least one hydroxide compound, the at least one hydroxide compound may be present in an amount generally ranging from 1% to 20% by weight relative to the total weight of the hydroxide composition, such as from 2% to 10% by weight.

According to the present invention, the at least one chelating acid may be at least one acid chosen from chelating agents and sequestering agents. The at least one chelating acid of the present invention comprises at least one group chosen from acid groups and salts thereof. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion, such as $Co^{2+}$, $Ni^{2+}$, $Cu^{2+}$, $Ca^{2+}$ or $Zn^{2+}$, is attached by coordinate links to two or more nonmetal atoms, i.e., ligands, in the same molecule. Non-limiting examples of chelating agents that may be used in the present invention include ethylenediaminetetraacetic acid (EDTA), nitrilotriacetic acid, ethyleneglycol-bis($\beta$-amino-ethyl ether)-N,N-tetraacetic acid, and salts of any of the foregoing.

Sequestering agents may be any material that prevents at least one ion from exhibiting its usual properties due to close combination with that material. See Zviak at 991. Non-limiting examples of sequestering agents that may be used in the present invention are hydroxy carboxylic acids, such as gluconic acid, citric acid, tartaric acid, and salts of any of the foregoing. In addition, other non-limiting examples of chelating agents and sequestering agents useful in the present invention include amino acids, crown ethers, and salts of any of the foregoing.

Further, the at least one chelating acid may be chosen from organic acids and salts thereof. In one embodiment, the at least one chelating acid is chosen from mono-hydroxycarboxylic acids, dihydroxycarboxylic acids, poly-hydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids, polyaminophosphonic acids, and salts of any of the foregoing.

In another embodiment, the at least one chelating acid is chosen from ethylene diamine tetraacetic acid (EDTA), N-(hydroxyethyl) ethylene diamine triacetic acid, aminotrimethylene phosphonic acid, diethylenetriamine-pentaacetatic acid, lauroyl ethylene diamine triacetic acid, nitrilotriacetic acid, iminodisuccinic acid, tartaric acid, citric acid, N-2-hydroxyethyliminodiacetic acid, and salts of any of the foregoing.

Depending on the nature of the at least one chelating acid, the solubility of the complex formed between the at least one chelating compound and the counter ion of the at least one hydroxide compound in the reaction medium may vary. In one embodiment, the at least one chelating compound-counter ion complex (metal chelate) is considered by one of ordinary skill in the art to be soluble in the reaction medium. In another embodiment, the present invention provides for an at least one chelating compound-counter ion complex having a solubility in water of greater than 0.03% at 25° C. and at a pH of 7.0, such as greater than 1% at 25° C. and at a pH of 7.0.

As one of ordinary skill in the art would recognize, mixtures of chelating acids including mixtures of at least one chelating agent and at least one sequestering agent are also within the practice of the invention. In one embodiment, a less active chelating acid may be mixed with a more active chelating acid, such as EDTA, to achieve a desired lanthionization of keratin fibers at a slower rate.

According to the present invention, the at least one carbonate compound may be chosen from inorganic carbonate salts and organic carbonate salts. Non-limiting examples of the at least one carbonate compound include sodium carbonate, potassium carbonate, potassium bicarbonate, and guanidine carbonate.

Further, the at least one carbonate compound may be completely dissociated by the at least one chelating acid, that is, the at least one carbonate compound may be completely converted to carbonic acid and a cationic counterion. According to the present invention, the molar ratio of the at least one chelating acid to the at least one carbonate compound in the inventive composition is greater than 0.2:1. In one embodiment, the molar ratio of the at least one chelating acid to the at least one carbonate compound is at least 0.3:1, such as greater than 0.3:1. In one embodiment, the molar ratio of the at least one chelating acid to the at least one carbonate compound is at least 0.4:1, such as greater than 0.4:1, while in another embodiment, the molar ratio of the at least one chelating acid to the at least one carbonate compound is at least 0.5:1, such as greater than 0.5:1. In another embodiment, the molar ratio of the at least one chelating acid to the at least one carbonate compound is at least 0.6:1, such as greater than 0.6:1, and in another embodiment, the molar ratio of the at least one chelating acid to the at least one carbonate compound is at least 0.7:1, such as greater than 0.7:1. In another embodiment, the molar ratio of the at least one chelating acid to the at least one carbonate compound is at least 0.8:1, such as greater than 0.8:1, and in another embodiment, the molar ratio of the at least one chelating acid to the at least one carbonate compound is at least 0.9:1, such as greater than 0.9:1. In one embodiment, the molar ratio of the at least one chelating acid to the at least one carbonate compound is at least 1:1, such as greater than 1:1, such as for example 2:1, 3:1, 4:1, 5:1 and all points in between.

The compositions of the present invention may further at least one solvent. Non-limiting examples of at least one solvent include water and organic solvents. Non-limiting examples of organic solvents include alkanols, such as ethanol, isopropanol, and ceteryl alcohol; glycerol; glycols and glycol ethers, such as 2-butoxyethanol, propylene glycol, propylene glycol monomethyl ether, diethylene glycol monoethyl and monomethyl ether, and aromatic alcohols, such as benzyl alcohol and phenoxyethanol, and mixtures thereof.

The present invention also provides for a multicomponent kit for lanthionizing keratin fibers comprising at least two compartments. One compartment of this kit comprises at least one carbonate compound and at least one chelating acid wherein the molar ratio of the at least one chelating acid to the at least one carbonate compound in the compartment is greater than 0.2:1. The second compartment comprises at least one hydroxide compound. For example, at least one component of at least one compartment may be activated by adding at least one suitable solvent.

The present invention also provides for a multicomponent kit for lanthionizing keratin fibers comprising at least three compartments. One compartment of this kit comprises at least one carbonate compound. A second compartment comprises an at least one chelating acid, and a third compartment comprises at least one hydroxide compound.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLES

General Procedure to Measure the Relaxing Efficiency of the Relaxers

Unless otherwise noted, the following procedure was used to measure the Relaxing Efficiency of the compositions comprising at least one activated hydroxide compound used for lanthionizing keratin fibers: At least one chelating acid and at least one carbonate compound were added to water. The amount of the at least one carbonate compound was stoichiometrically equivalent to the amount of the at least one chelating acid such that all of the at least one carbonate compound and the at least one chelating acid were converted to carbonic acid gas and chelating compound, respectively. After the effervescence ceased, the solution was added to a hydroxide composition comprising at least one hydroxide compound (a calcium hydroxide cream), and the mixture was mixed for 3 minutes. The resulting mixture (an activated hydroxide composition) was then applied to a natural kinky hair swatch that was stretched and taped in a straight configuration. The mixture was worked into the hair for 5 minutes and the treated hair swatch was allowed to stand at ambient temperature for another 15 minutes. The hair swatch was rinsed and shampooed, and then placed in a humidity chamber at 90% Relative Humidity for 24 hours. The % Relaxing Efficiency (% RE) is defined as:

$$\% RE = (L_f/L_t) \times 100$$

wherein $L_f$=Length of the relaxed hair after 24 hours at 90% Relative Humidity; and $L_t$=Length of the hair at the straight configuration.

A typical 5% calcium hydroxide cream is shown as follows:

| Materials | Amount (% w/w) |
|---|---|
| Cetyl alcohol | 1.0 |
| Steareth-2 | 0.5 |
| Steareth-10 | 2.5 |
| Mineral Oil | 15.0 |
| Petrolatum | 5.5 |
| Cetearyl alcohol and Cetearyl Phosphate | 7.5 |
| Propylene Glycol | 3.0 |
| Calcium Hydroxide | 5.0 |
| Water | 60.0 |

Example 1

Generation of Hydroxide Ions using a Carbonate Compound, a Chelating Acid and Calcium Hydroxide A stoichiometric amount of a solid chelating acid (as shown in Table 1) was added to a solution containing a carbonate compound (as shown in Table 1). The resulting composition was stirred until bubbling stopped. Calcium hydroxide (1–2 g) was then added to the composition, and the slurry was stirred for 10–15 minutes. The pH was measured after each step of the process. The results are shown in Table 1.

TABLE 1

Measurement of the Change in pH of the Carbonate/Chelating Acid/Calcium Hydroxide Process

| Carbonate (Amount) | pH of Carbonate Solution | Chelating Acid (Amount) | pH of Activator Composition | pH After Mixing Activator Composition with Ca(OH)$_2$ |
|---|---|---|---|---|
| KHCO$_3$ (0.82 g/5 g water) | 8.31 | Na$_2$EDTA (1.51 g) | 7.05 | 13.5 |
| Guanidine Carbonate (1.09 g/3 g water) | 11.77 | Citric Acid (0.78 g) | 5.25 | 13.25 |
| K$_2$CO$_3$ (0.84 g/2 g water) | 12.55 | Citric Acid (0.78 g) | 5.72 | 13.75 |

The results showed that, unlike conventional activators which have a high pH (typically ranging from 11 to 12), the compositions of the present invention had a low pH and were still able to generate hydroxide ions as indicated by the high pH (above 13) after mixing with calcium hydroxide.

Example 2

Hair Relaxer Composition using Composition Formed from Tartaric Acid and Sodium carbonate Following the general procedure, natural kinky hair was relaxed with a composition comprising at least one activated hydroxide compound formed from a composition comprising 0.97 g tartaric acid (chelating acid) and 0.69 g Na$_2$CO$_3$ (carbonate compound) in 3 g water, and 6 g of an 8% calcium hydroxide cream (hydroxide composition). The molar ratio of the chelating acid to calcium hydroxide was 1:1. The % RE was 89.

Example 3

Hair Relaxer Composition using Composition Formed from Nitrolotriacetic Acid and Sodium Carbonate Following the above procedure, natural kinky hair was relaxed with a composition comprising at least one activated hydroxide compound generated from a composition comprising 1.24 g nitrilotriacetic acid (NTA) (chelating acid) and 1.03 g $Na_2CO_3$ in 3 g of water, and 6 g of an 8% calcium hydroxide cream. The molar ratio of chelating acid to calcium hydroxide was 1:1. The % RE was 65.

Example 4

Efficiency of Hair Relaxer Compositions using Composition Formed from Disodium EDTA and Potassium Bicarbonate Following the above procedure, a composition was generated by adding 1.51 g $Na_2$EDTA to a solution of 0.81 g $KHCO_3$ in 5 g of water. The mixture was stirred until there were no bubbles coming out of the solution. This composition was then added to a hydroxide composition (12 g) that contained from 6% to 8% calcium hydroxide. The results are shown in Table 2.

TABLE 2

Relaxing Efficiency of $Na_2$EDTA/$KHCO_3$/$Ca(OH)_2$ Relaxers

| Concentration of $Ca(OH)_2$ in Hydroxide Composition (%) | Molar Ratio of Chelating Acid:$Ca(OH)_2$ | % RE |
|---|---|---|
| 6 | 1.0:0.42 | 60 |
| 7 | 1.0:0.36 | 77 |
| 8 | 1.0:0.31 | 71 |

The data showed that relaxers formed from a calcium hydroxide cream and a composition comprising $Na_2$EDTA and $KHCO_3$ can straighten natural kinky hair.

Example 5

Efficiency of Composition Formed from Citric Acid and Guanidine Carbonate as a Function of the Molar Ratio of Chelating Acid to Calcium Hydroxide Following the above procedure, a composition was generated by adding 0.78 g of citric acid to a solution of 1.1 g guanidine carbonate in 3 g of water. The mixture was stirred until there were no bubbles coming out of the solution. This composition was then added to a hydroxide composition (6 g) that contained from 5% to 8% calcium hydroxide. The results are shown in Table 3.

TABLE 3

Relaxing Efficiency of Citric Acid/Guanidine Carbonate/$Ca(OH)_2$ Relaxers

| Concentration of $Ca(OH)_2$ in Hydroxide Composition (%) | Molar Ratio of Chelating Acid:$Ca(OH)_2$ | % RE |
|---|---|---|
| 5 | 1.0:1.0 | 62 |
| 6 | 1.0:0.84 | 66 |
| 7 | 1.0:0.72 | 87 |
| 8 | 1.0:0.63 | 97 |

The data showed that relaxers formed from a calcium hydroxide cream and a composition comprising citric acid and guanidine carbonate can straighten natural kinky hair.

Example 6

Efficiency of Composition Formed from Citric Acid and Potassium Carbonate and Hydroxide Following the above procedure, a composition was generated by adding 0.78 g of citric acid to a solution of 0.84 g potassium carbonate ($K_2CO_3$) in 2 g of water. The mixture was stirred until there were no bubbles coming out of the solution. This composition was then added to a hydroxide composition (6 g) that contained 6% to 8% calcium hydroxide. The results are shown in Table 4.

TABLE 4

Relaxing Efficiency of Citric acid/$K_2CO_3$/$Ca(OH)_2$ Relaxers

| Concentration of $Ca(OH)_2$ in Hydroxide Composition (%) | Molar Ratio of Chelating Acid:$Ca(OH)_2$ | % RE |
|---|---|---|
| 6 | 1.0:0.84 | 67 |
| 7 | 1.0:0.72 | 70 |
| 8 | 1.0:0.63 | 88 |

The data showed that relaxers that consist of a calcium hydroxide cream and a composition comprising citric acid and potassium carbonate can straighten natural kinky hair. Better relaxing efficiency resulted from higher calcium hydroxide creams.

Example 7

Efficiency of Hair Relaxers using Composition Formed from Citric Acid and Potassium Carbonate Following the above procedure, a composition was generated by adding a solid mixture of citric acid and potassium carbonate ($K_2CO_3$) to 2 g of water. The mixture was stirred until there were no bubbles coming out of the solution. This composition was then added to a hydroxide composition comprising from 5% to 8% calcium hydroxide. The amount of calcium hydroxide cream that was used is equivalent to 0.48 g–0.50 g of available calcium hydroxide. The resulting relaxer mixtures had a chelating acid:calcium hydroxide molar ratio of 1:1. The results are shown in Table 5.

TABLE 5

Relaxing Efficiency of citric acid/$K_2CO_3$/$Ca(OH)_2$ Relaxers

| Concentration of $Ca(OH)_2$ in Hydroxide Composition (%) | Amount of $Ca(OH)_2$ Cream (g) | Amount of Citric Acid (g) | Amount of $K_2CO_3$ (g) | % RE |
|---|---|---|---|---|
| 5 | 10 | 1.29 | 1.40 | 70 |
| 6 | 8 | 1.24 | 1.34 | 86 |
| 7 | 7 | 1.27 | 1.37 | 96 |
| 8 | 6 | 1.24 | 1.34 | 93 |

The data showed that relaxers formed from a calcium hydroxide cream and a composition comprising citric acid and $K_2CO_3$ can straighten natural kinky hair. When the molar ratio of the chelating acid:calcium hydroxide is 1:1 and the available calcium hydroxide is the same in the relaxer, the relaxing efficiency was better as the concentration of the calcium hydroxide increased.

Example 8

Efficiency of Hair Relaxers using Compositions Formed from Citric Acid and Potassium Carbonate Following the above procedure, a composition was generated by adding a solid mixture of citric acid and potassium carbonate ($K_2CO_3$) to 2.5 g of water. The mixture was stirred until there were no bubbles coming out of the solution. This composition was then added to a hydroxide composition (6 g) that contained 8% calcium hydroxide. The results are shown in Table 6.

TABLE 6

Relaxing Efficiency of citric acid/$K_2CO_3$/Ca(OH)$_2$ Relaxers

| Amount of Citric Acid Cream (g) | Molar ratio of Chelating Acid:Ca(OH)$_2$ | Amount of $K_2CO_3$ (g) | % RE |
|---|---|---|---|
| 0.25 | 1.0:0.2 | 0.35 | 43 |
| 0.5 | 1.0:0.4 | 0.70 | 65 |
| 0.75 | 1.0:0.6 | 1.05 | 82 |
| 1.0 | 1.0:0.8 | 1.40 | 89 |
| 1.24 | 1.0:1.0 | 1.75 | 92 |
| 1.49 | 1.0:1.2 | 2.10 | 93 |

The data showed that relaxers formed from a calcium hydroxide cream and a composition comprising citric acid and $K_2CO_3$ can straighten natural kinky hair. When 8% calcium hydroxide cream was used, the relaxing efficiency increased as the molar ratio of the chelating acid:calcium hydroxide increased.

Example 9

Efficiency of Hair Relaxers using Composition Formed from Citric Acid/Citrate and Potassium Carbonate Following the above procedure, a composition was generated by adding a solid mixture of citric acid/potassium citrate and potassium carbonate ($K_2CO_3$) to 2 g of water. The amount of citric acid in the mixture increased from 0% to 100%. The chelating compound:calcium hydroxide molar ratio was 1.0:0.8. The mixture was stirred until there were no bubbles coming out of the solution. This composition was then added to a hydroxide composition (6 g) that contained 8% calcium hydroxide. The results are shown in Table 7.

TABLE 7

Relaxing Efficiency of Citric acid/Citrate/$K_2CO_3$/Ca(OH)$_2$ Relaxers

| Amount of Citric Acid (g) | Amount of Potassium Citrate (g) | Amount of $K_2CO_3$ (g) | % RE |
|---|---|---|---|
| 1.00 | 0 | 1.07 | 97 |
| 0.70 | 0.5 | 0.75 | 91 |
| 0.50 | 0.84 | 0.54 | 96 |
| 0.30 | 1.18 | 0.32 | 95 |
| 0 | 1.68 | 0 | 98 |

The data showed that relaxers formed from a calcium hydroxide cream and a composition comprising citric acid/citrate/$K_2CO_3$ can straighten natural kinky hair.

What is claimed is:

1. A method for lanthionizing keratin fibers to achieve relaxation of said keratin fibers comprising:
   (a) generating a composition comprising at least one chelating compound by reacting:
      (i) at least one carbonate compound; and
      (ii) at least one chelating acid,
   wherein the molar ratio of said chelating acid to said carbonate compound is greater than 0.2:1;
   (b) generating at least one activated hydroxide composition by reacting said composition comprising at least one chelating compound with at least one hydroxide compound;
   (c) applying said at least one activated hydroxide composition to said keratin fibers for a sufficient period of time to lanthionize said keratin fibers; and
   (d) terminating said lanthionization.

2. The method according to claim 1, wherein said at least one hydroxide compound is reacted with said composition following release of carbonic acid gas that is formed from the reacting of said at least one carbonate compound and said at least one chelating acid.

3. The method according to claim 1, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, and Group VI hydroxides, organic hydroxides.

4. The method according to claim 3, wherein said at least one hydroxide compound is chosen from calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

5. The method according to claim 4, wherein said at least one hydroxide compound is calcium hydroxide.

6. The method according to claim 1, the molar ratio of said at least one chelating acid to said at least one hydroxide compound is at least 1:0.2.

7. The method according to claim 1, the molar ratio of said at least one chelating acid to said at least one hydroxide compound is at least 1:0.5.

8. The method according to claim 1, the molar ratio of said at least one chelating acid to said at least one hydroxide compound is at least 1:1.

9. The method according to claim 1, wherein at least one hydroxide composition comprises said at least one hydroxide compound.

10. The method according to claim 9, wherein said at least one hydroxide composition is in the form of a solution, an emulsion, a suspension, a solid, a cream, a gel, a paste or a foam.

11. The method according to claim 1, wherein said at least one hydroxide composition further comprises at least one additive.

12. The method according to claim 11, wherein said at least one additive is chosen from solvents, anionic surfactants, cationic surfactants, nonionic surfactants, amphoteric surfactants, zwitterionic surfactants, thiol compounds, fragrances, silicones, silicone derivatives, screening agents, preserving agents, proteins, vitamins, polymers, plant oils, mineral oils, and synthetic oils.

13. The method according to claim 12, wherein said solvents are chosen from water and organic solvents.

14. The method according to claim 13, wherein said organic solvents are chosen from alkanols, glycerol, glycols, glycol ethers, aromatic alcohols, and mixtures thereof.

15. The method according to claim 9, wherein said at least one hydroxide compound is present in an amount ranging from 1% to 20% by weight relative to the total weight of said at least one hydroxide composition.

16. The method according to claim 15, wherein said at least one hydroxide compound is present in an amount ranging from 2% to 10% by weight relative to the total weight of said at least one hydroxide composition.

17. The method according to claim 1, wherein said at least one chelating acid is chosen from is chosen from organic acids and salts thereof.

18. The method according to claim 1, wherein said at least one chelating acid is chosen from aminocarboxylic acids, hydroxycarboxylic acids, aminosulfonic acids, hydroxysulfonic acids, aminophosphonic acids, hydroxyphosphonic acids, and salts of any of the foregoing.

19. The method according to claim 1, wherein said at least one chelating acid is chosen from ethylene diamine tetraacetic acid, N-(hydroxyethyl) ethylene diamine triacetic acid, aminotrimethylene phosphonic acid, diethylenetriaminepentaacetic acid, lauroyl ethylene diamine triacetic acid, nitrilotriacetic acid, iminodisuccinic acid, tartaric acid, citric acid, N-2-hydroxyethyliminodiacetic acid, and salts of any of the foregoing.

20. The method according to claim 1, wherein a complex is formed between said at least one chelating compound and at least one counterion of said at least one hydroxide compound, wherein said complex has a solubility in water of greater than 0.03% at 25° C. and a pH of 7.0.

21. The method according to claim 1, wherein a complex is formed between said at least one chelating compound and at least one counterion from said at least one hydroxide compound, wherein said complex has a solubility in water of greater than 1% at 25° C. and a pH of 7.0.

22. The method according to claim 1, wherein said at least one carbonate compound is chosen from inorganic carbonates and organic carbonates.

23. The method according to claim 22, wherein said at least one carbonate compound is chosen from sodium carbonate, potassium carbonate, potassium bicarbonate and guanidine carbonate.

24. The method according to claim 1, wherein the molar ratio of said at least one chelating acid to said at least one carbonate compound is at least 0.5:1.

25. The method according to claim 1, wherein the molar ratio of said at least one chelating acid to said at least one carbonate compound is at least 0.6:1.

26. The method according to claim 1, wherein said composition further comprises at least one solvent.

27. The method according to claim 26, wherein said at least one solvent is water.

28. The method according to claim 1, wherein at least one carbonate composition comprises said at least one carbonate compound.

29. The method according to claim 1, wherein at least one carbonate composition further comprises at least one solvent.

30. The method according to claim 29, wherein said at least one solvent is water.

31. The method according to claim 1, wherein said keratin fibers are hair.

32. The method according to claim 1, further comprising rinsing said keratin fibers with water after said terminating of said lanthionization.

33. A method according to claim 1, wherein said lanthionization is terminated when a desired level of relaxation of the keratin fibers has been reached.

34. A method of generating an activated hydroxide compound comprising:
  (a) generating a composition comprising at least one chelating compound by reacting:
    (i) at least one carbonate compound; and
    (ii) at least one chelating acid,
  wherein the molar ratio of said at least one chelating acid to said at least one carbonate compound is greater than 0.2:1; and
  (b) reacting said composition comprising at least one chelating compound with at least one hydroxide compound.

35. A multicomponent kit for lanthionizing keratin fibers comprising at least two compartments,
  wherein a first compartment comprises at least one carbonate compound and at least one chelating acid, wherein the molar ratio of said at least one chelating acid to said at least one carbonate compound is greater than 0.2:1; and
  wherein a second compartment comprises at least one hydroxide compound.

36. A multicomponent kit for lanthionizing keratin fibers comprising at least three compartments,
  wherein a first compartment comprises at least one carbonate compound;
  wherein a second compartment comprises at least one chelating acid; and
  wherein a third compartment comprises at least one hydroxide compound.

* * * * *

UNITED STATES PATENT AND TRADEMARK OFFICE
CERTIFICATE OF CORRECTION

PATENT NO. : 6,800,277 B2
DATED : October 5, 2004
INVENTOR(S) : Van Nguyen et al.

Page 1 of 1

It is certified that error appears in the above-identified patent and that said Letters Patent is hereby corrected as shown below:

<u>Column 14,</u>
Line 14, "and Group VI hydroxides, organic" should read -- Group VI hydroxides, and organic --.
Line 64, "acid is chosen from is chosen from organic" should read -- acid is chosen from organic --.

Signed and Sealed this

Eighth Day of February, 2005

JON W. DUDAS
*Director of the United States Patent and Trademark Office*